(12) United States Patent
Miller et al.

(10) Patent No.: US 8,616,068 B2
(45) Date of Patent: Dec. 31, 2013

(54) ARRAY FOR SENSING AND INDUCING STRAIN IN AN ADHESIVELY BONDED JOINT INCLUDING MAGNETOSTRICTIVE MATERIAL

(75) Inventors: Robert J. Miller, Fall City, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 1 day.

(21) Appl. No.: 13/556,504

(22) Filed: Jul. 24, 2012

(65) Prior Publication Data

US 2013/0081475 A1  Apr. 4, 2013

Related U.S. Application Data

(62) Division of application No. 12/169,768, filed on Jul. 9, 2008, now Pat. No. 8,250,928.

(51) Int. Cl.
*G01L 1/00* (2006.01)

(52) U.S. Cl.
USPC .......................................................... 73/779

(58) Field of Classification Search
USPC .......................................................... 73/779
See application file for complete search history.

(56) References Cited

U.S. PATENT DOCUMENTS

| | | | |
|---|---|---|---|
| 4,004,456 A * | 1/1977 | Vahaviolos | 73/801 |
| 4,924,711 A | 5/1990 | Reilly | |
| 6,433,463 B1 * | 8/2002 | Lal et al. | 310/328 |
| 7,669,467 B2 * | 3/2010 | Breuer et al. | 73/150 A |
| 2005/0068041 A1 | 3/2005 | Kress | |
| 2007/0100582 A1 | 5/2007 | Griess et al. | |

FOREIGN PATENT DOCUMENTS

| | | |
|---|---|---|
| EP | 0594180 A2 | 4/1994 |
| WO | 2006062275 A1 | 6/2006 |

* cited by examiner

*Primary Examiner* — Lisa Caputo
*Assistant Examiner* — Octavia Davis-Hollington
(74) *Attorney, Agent, or Firm* — Hugh P. Gortler

(57) ABSTRACT

Sensing strain in an adhesively bonded joint includes inducing a strain wave in the joint, and sensing a change in local magnetic characteristics in the joint. An array includes a plurality of elements for sensing and inducing a strain wave in selected regions of a structure having the adhesively bonded joint. The elements include at least one micromechanical driver for inducing strain waves in selected regions, a plurality of mechanical sensors for measuring vibrations resulting from the induced strain waves, a plurality of micromagnetic drivers for generating weak magnetic fields over the selected regions, and a plurality of micromagnetic sensors for sensing magnetic responses of the selected regions to the strain waves.

9 Claims, 9 Drawing Sheets

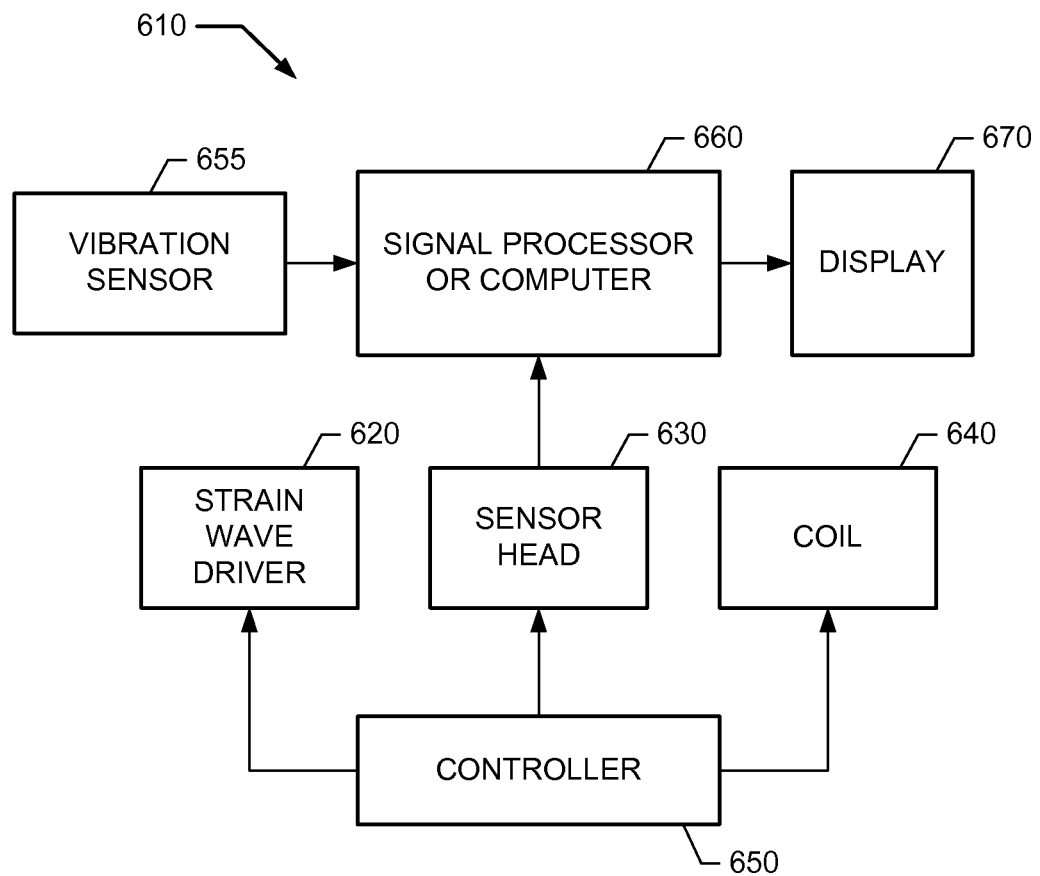

ARRAY FOR SENSING AND INDUCING STRAIN IN AN ADHESIVELY BONDED JOINT INCLUDING MAGNETOSTRICTIVE MATERIAL

This is a divisional of copending U.S. Ser. No. 12/169,768 filed Sept. 4, 2007.

BACKGROUND

Lightweight composite materials hold great promise for the aircraft industry. Fiber composites provide a significant improvement in specific strength and stiffness over conventional metal alloys. Better specific strength and stiffness translates into weight savings, which translates into fuel savings and lower operating costs. Additionally, composites do not corrode like aluminum, and they are more resistant to fatigue.

Composite elements such as skins, stiffeners, frames and spars are joined together to form major components such as wings, fuselage and empennage. The composite elements may be bonded together with polymeric adhesive. In theory, adhesive bonds alone have sufficient strength and integrity to support loading of these components. Therefore, adhesive bonds should be able to greatly reduce the number of metal fasteners in the major components.

In practice, however, certain federal aviation regulations require substantiation that a bonded joint between any two primary structural components will carry a specified load with a maximum disbond (that is, where an entire bond line is missing). One solution to this lack of confidence in adhesively bonded joints has been to add metal fasteners. In the event an adhesively bonded joint fails, a metal fastener would continue holding the joint together.

The use of metal fasteners adds weight to aircraft components. The use of metal fasteners with composite structures also increases the time, cost and complexity of fabrication. High precision machines and complex procedures are used to drill through composite structures. Moreover, penetrations for fasteners provide unwanted paths for lightning strike and corrosion.

Weight is also added by plies of composite that are added around the drilled holes to satisfy requirements for by-pass bearing loads. The presence of fastener holes also forces the selection of composite ply layup orientations that reduce the strength of panels and bonded joints (as compared to optimally designed panels and joints without fasteners).

It is believed that adhesive bonds alone, if properly designed, prepared and controlled, have sufficient strength and integrity to bond primary structures together. However, data proving consistency and reliability is unavailable, Data about an adhesive bond can be gathered by measuring strain in the adhesive bond. The distribution of strain in the adhesive can be affected by weak bonds and other structural inconsistencies.

It would be desirable to increase the sensitivity of sensing the strain in an adhesively bonded joint.

SUMMARY

According to an embodiment herein, a method of sensing strain in an adhesively bonded joint includes inducing a strain wave in the joint, and sensing a change in local magnetic characteristics in the joint.

According to an embodiment herein, an array includes a plurality of elements for sensing and inducing a strain wave in selected regions of a structure having an adhesively bonded joint. The elements include at least one micromechanical driver for inducing strain waves in selected regions, a plurality of micromagnetic drivers for generating weak magnetic fields over the selected regions, and a plurality of micromagnetic sensors for sensing magnetic responses of the selected regions to the strain waves.

BRIEF DESCRIPTION OF THE DRAWINGS

FIG. 6 is an illustration of a system for sensing strain in a structure having an adhesively bonded joint.

DETAILED DESCRIPTION

Figure 1:
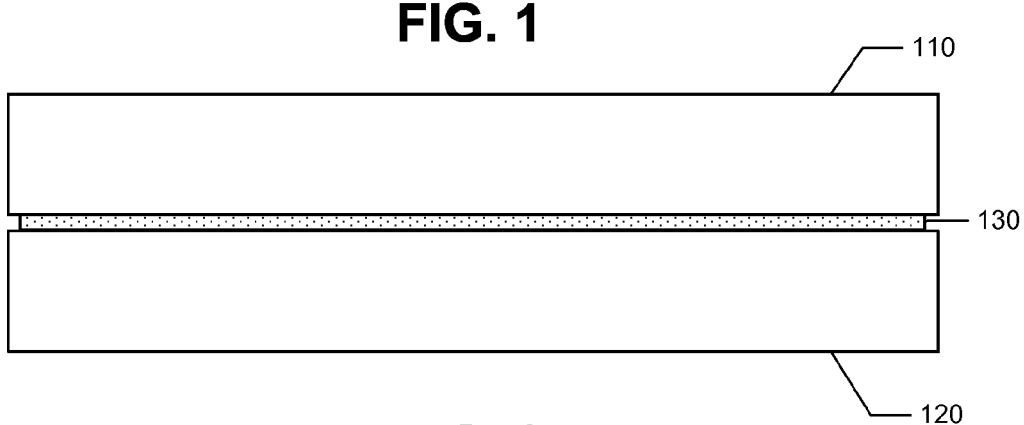
FIG. 1 is an illustration of a structure having an adhesively bonded joint.

Reference is made to FIG. 1. First and second structures 110 and 120 are bonded together with an adhesive 130 to form a bonded joint. The adhesive 130 may be a thermosetting polymer or a thermoplastic polymer. The adhesive 130 may contain additional materials such as fiber mats (scrim) or other fillers. The adhesive 130 may form a bond line, a fillet, a sealant, a covering on a panel, etc. The adhesive 130 may be used for bonding primary or non-primary structures.

The adhesive 130 includes strain-sensitive magnetostrictive material. Magnetostriction is a property of ferromagnetic material that causes the ferromagnetic material to change their shape when subjected to a magnetic field. Conversely, subjecting magnetostrictive material to any level of physical strain (down to a few microstrains or better) produces a change in the magnetic domain structure, which changes the characteristic way the material magnetizes when a small magnetic field is applied. These changes are measurable.

The level of strain in the adhesive 130 provides an indicator of the strength of adhesion between the adhesive 130 and the structures 110 and 120. Strain in the adhesive 130 develops as the result of chemical and physical changes occurring during polymerization and as the result of coefficient of thermal expansion differences between the adhesive 130 and the structures 110 and 120. The strain in the adhesive 130 can be predicted by finite element analysis. If the bonded joint is without irregularities, the strain map of the bonded joint should match the finite element analysis. Higher or lower levels of adhesive strain (as compared to the finite element analysis) will appear in areas within the structure-adhesive interfaces that are in direct contact, but not able to transfer the load without dimensional change (i.e., through a lower modulus material). This will result in a localized measurable change in the magnetic characteristics between the localized area and any of a) the strains at other areas, b) computed or expected strains, c) the same area at another time, and d) the same area after damage. Higher or lower strain levels indicate the presence or predisposition for structural inconsistencies such as disbonds, delaminations, and localized cavitation (ranging in size from ten microns to the entire joint).

By measuring localized differences in magnetic properties, strains that characterize structural inconsistencies can be located. For instance, "kissing disbonds" occur where the adhesive 130 and structure surfaces are in contact, but load is not transferred across the interface under loading of the joint. Kissing disbonds may occur due to the presence of low modulus regions of contaminants such as siloxane release agents.

The magnetostrictive material is not limited to any particular composition. In some embodiments, the magnetostrictive material may include magnetic metal oxides such as magnetite, amorphous metals, and ferromagnetic metals and alloys such as nickel-iron (NiFe). In some embodiments, the magnetostrictive material may also include ferrites or oxides of ferromagnetic metals or alloys.

In some embodiments, the magnetostrictive material may include Terfenol-D. Terfenol-D is an alloy of terbium, dysprosium, and iron metals. It is a solid-state transducer capable of converting very high energy levels from one form to another. In the case of electrical-to-mechanical conversion, the magnetostriction of Terfenol-D generates strains ten to twenty times greater than traditional magnetostrictive materials such as iron-cobalt alloys, and two to five times greater than traditional piezoceramics. Terfenol-D has a high Curie temperature (380° C.), which enables magnetostrictive performance greater than 1000 ppm from room temperature to 200° C.

Common service temperatures of an aircraft might be in the range from −65° F. to 300° F., with some resin systems being used outside of this range. Some parts of an aircraft may remain hot even when flying at altitude due to proximity to engines or heat given off by internal aircraft systems in confined areas.

In some embodiments, the magnetostrictive material may include Galfenol, which is an iron-gallium alloy that has physical and magnetic properties that are distinctly different than those of Terfenol-D. While Galfenol's magnetostriction is only a third to a quarter that of Terfenol-D, Galfenol is a much more robust material, allowing it to be used in mechanically harsh environments with minimal shock hardening.

Thickness of the adhesive 130 will depend upon the structures being bonded. For instance, a bond line may have a thickness of about 10 mils.

The magnetostrictive material may have a form ranging from nanoparticles to films. Particles such as flakes, fiber shapes and coated fibers typically have higher coupling of strains between the adhesive 130 and the magnetic particle than spherical or cubic-like shapes, and therefore are desirable. Particle size and film thickness may be determined by the size and thickness limits allowed by the adhesive 130. However, particle dimensions should be small enough to minimize adverse affects on adhesive structural properties. Still, there is a wide range of useful particle dimensions depending on the shape, ranging from nanometers to microns. Magnetostrictive film thicknesses may range from nanometers to a few microns.

Proportion of the magnetostrictive material to adhesive 130 may be in the range of 0.1% to 30% by volume. However, lower proportions in the range of 0.1% to 1% volume are desirable for adhesive mechanical performance and lower weight.

Strain in a bonded joint causes strain in the magnetostrictive material. This strain, in turn, produces measurable changes in the magnetization of the magnetostrictive material.

Figure 2:
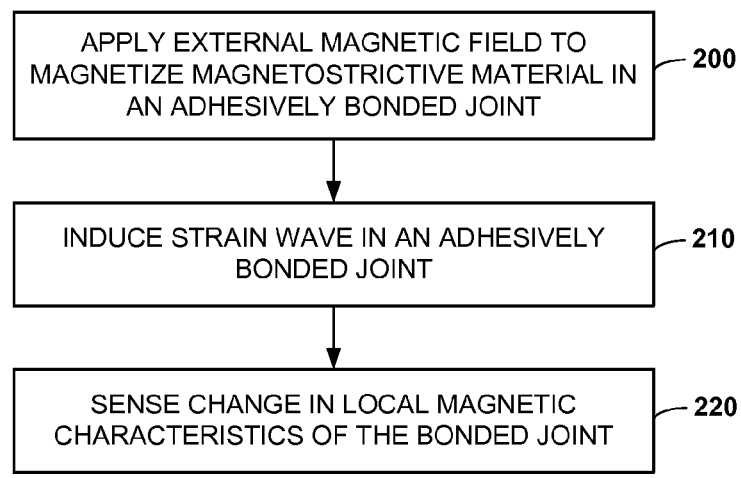
FIG. 2 is an illustration of a method of sensing strain in a structure having an adhesively bonded joint.

Reference is now made to FIG. 2, which illustrates a method of sensing strain in an adhesively bonded joint including strain-sensitive magnetostrictive material. At block 200, a weak external magnetic field may be applied to the bonded joint. The weak external magnetic field produces a weak sinusoidal field. In response, the magnetostrictive material becomes partially or wholly magnetized.

At block 210, a strain wave is induced in the bonded joint. A longitudinal or transverse wave may be induced. As a result, the bonded joint is subjected to a vibration. The vibration, a time varying stress that propagates through the structure, induces a time-varying change to the magnetic properties of magnetostrictive material. The strain wave propagates through the structure, at each point in the bonded joint, causing the local residual stress/strain and magnetization to change.

A strain wave may be applied as a single pulse or a repeated stress/strain pulse. The magnetic effects of each pulse on the magnetostrictive material are transient and decay.

Figure 3:
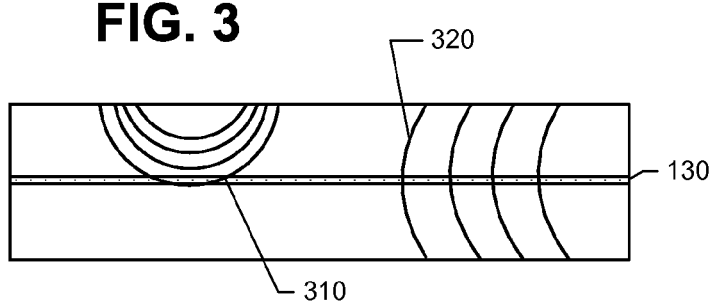
FIG. 3 is an illustration of a strain wave propagating through a structure having an adhesively bonded joint.

Additional reference is made to FIG. 3, which illustrates the external magnetic field lines 310 and the strain wave 320 propagating along the adhesively bonded joint 130 (in other embodiments, the strain wave can be propagated across the joint 130). The field that passes through the adhesive is affected by strain. If a sensor is placed over the field lines 310 and a source provides a dH/dt field, sensor voltage is roughly $dB(H, \sigma)_{(at\ sensor)}/dt$. $B_{at\ sensor}$ and depends on integration of B along field lines (analogous to an electric current dependence on the sum of all the resistances along the path). Selection of source frequency and spacing between sensor and source determine depth of field lines and resolution.

The specific effect of the strain wave is to change the magnetic anisotropy of the magnetostrictive material (analogous to a mechanical spring constant), which in turn changes the way the material is magnetized by the external magnetic field. The slope of the magnetization versus the external magnetic field is the magnetic permeability. Since the external magnetic field is sinusoidal, the sensor measures the sinusoidal dependence of the magnetization on the external magnetic field in the form of what is commonly called a BH loop. The slope (the permeability) is dependent on the strain.

At block 220, a change in local magnetic characteristics in the joint is sensed. The local magnetization may be measured at points along the joint. Each sensor looks at localized change of a location of the joint. For example, at each location a sensor may sense a rate of change of magnetic induction (dB/dt).

In some embodiments, measurements of magnetization are made only in the direction of the strain wave. In other embodiments, measurements may also be made in directions orthogonal to the direction of the strain wave. The effect may be as large in orthogonal directions but according to Poisson's ratio should have a different sign. Because waves in a solid can be longitudinal or transverse, the magnetostriction effect (although one wave travels faster than the other so may be able to separate in time) may be complex.

A magnetic sensor array may be used to create a strain image of the joint. In some structures, however, the sensor array might not be large enough to inspect an entire joint. Therefore, the sensor array may be moved to different locations of the joint. For example, initial inspections may be made areas of known or predicted sensitivity to defects such as stress concentrating sharp angles and near edges.

The strain wave has been found to improve the sensitivity of sensing the strain. The strain wave improves the magnetic response of the magnetostrictive material beyond that due to thermal residual strain. A strain wave increases the magnetic effect of defects. That is, defect signatures are amplified by application of the strain wave. The sensitivity of this sensing is improved even for incidental variations in geometry, material properties and especially to variations in the residual strain in a bonded joint.

Some types of weak bonds can potentially be detected because the induced strain in the adhesive is sensitive to the modulus of adjacent materials such as low modulus contaminants. A method herein could also be used as a local proof test if high energy vibrations or loading is done and plastic strains in weak bonds are sensed. In addition, small disbonds may be detected using an array of very small magnetic sensors that measure localized fields.

The frequency and amplitude of the vibration of the strain wave may be selected so as not to push the bonded joint into the plastic regime. A safe maximum strain may be on the order of 1000 microstrains. The amplitude should produce time varying strains that are large enough (at least one microstrain) to produce measurable magnetic effects.

In some embodiments, the strain may be applied as a continuous wave. The continuous wave in combination with the external magnetic field allows for integration of the measurements over time and increased sensitivity and noise rejection. In other embodiments, the strain may be applied as a pulse, and the ring-down time (the time it takes for the magnetic effects to disappear) may be used to characterize the bonded joint.

The frequency may be any frequency for which mechanical waves will propagate in the adhesive. Use of high frequencies that only penetrate a small distance into the adhesive may be used to limit the area that is being inspected. Frequency of the strain wave may be varied to inspect the structure at different depths.

Figure 4:
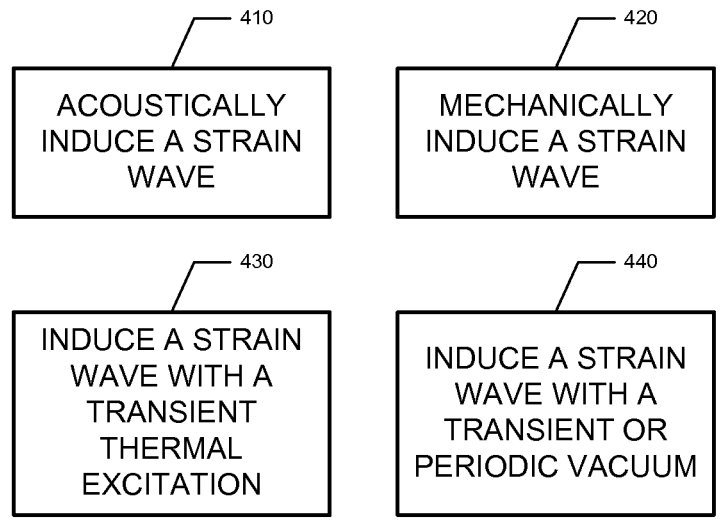
FIG. 4 is an illustration of various ways of inducing a strain wave in an adhesively bonded joint.

Reference is now made to FIG. 4, which illustrates different ways of inducing a strain wave in an adhesively bonded joint. In some embodiments (block 410), the strain wave may be induced acoustically (e.g., by ultrasonic waves). In other embodiments (block 420) the strain wave may be induced mechanically (e.g., an attached vibrator). In other embodiments (block 430), the strain wave may be induced with a transient thermal excitation (e.g. a flash lamp). In still other embodiments (block 440), the strain wave may be induced with a transient or periodic vacuum (e.g. a vacuum head or chamber). A driver for inducing a strain wave may include, for example, any of mechanical impedance devices, acoustic horns, piezoelectric transducers, lasers, electromagnetic pulsers, transient or periodic vacuum sources, or transient thermal sources.

Figure 5A:
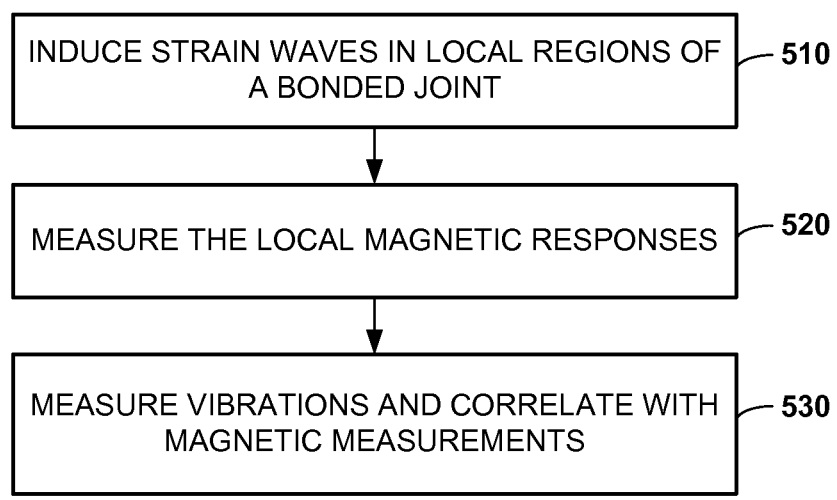
FIGS. 5*a*-5*c* are illustrations of methods of assessing structural health of a structure having an adhesively bonded joint.
Figure 5B:
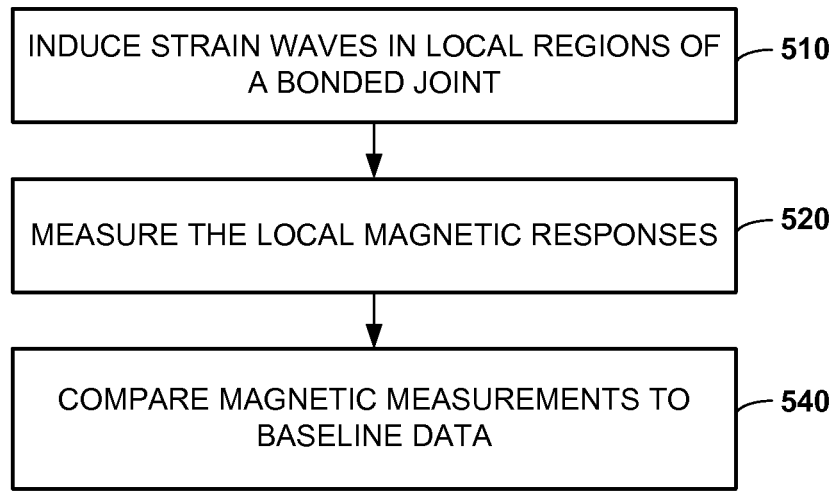
Figure 5C:
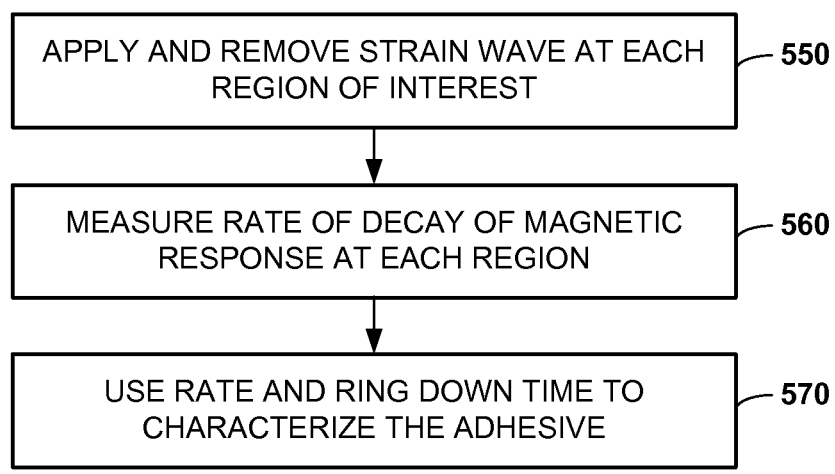

FIGS. 5a-5c illustrate methods of assessing structural health of structure having an adhesively bonded joint. In the method of FIG. 5a, a strain wave is induced in local regions of the joint (block 510). The induced strain and magnetic properties depend on the local adhesive mechanical properties. Adhesive adjacent to a disbond or weak bond will have anomalous strain, and therefore produce a different magnetic response than areas of good bond.

At block 520, the local magnetic responses at the local regions are measured as the strain is being induced.

At block 530, the mechanical vibrations at the regions are measured and correlated with the magnetic measurements.

The location of structural inconsistencies can be determined by sensing and correlating both the magnetic and mechanical vibrations due to the vastly different speeds of propagation of mechanical and magnetic waves. This correlation increases sensitivity, for example, to weak bonds and reduces sensitivity to other non-structural effects. The correlation of the strain wave and magnetic signals should select only the induced strain (thereby indicating the bond strength).

Magnetic effects that are not due to strains (such as variability in the adhesive thickness or in the separation between the sensors and the adhesive) may be selected out. For example, magnetic effects not due to strains may be selected out by subtracting out the magnetic measurement taken without the strain applied.

In the method of FIG. 5b, strain waves are induced at local regions of a bonded joint (block 510), the local magnetic responses at the regions are measured (block 520), and the magnetic measurements are compared to baseline data (block 540). The baseline data could include previous measurements of the magnetization, or expected data representing a good bond. For instance, the expected data could be obtained from Finite Element analysis of the structure.

In the method of FIG. 5c, a strain wave is applied to and then removed from each region of interest (block 550) after which the rate of decay of the magnetic response at each region is measured (block 560). This rate may be sensitive to defects or plastic deformation that indicates weak bonds. Thus, the rate and ring down time (the time it takes for the magnetic effects to disappear) may be used to characterize the adhesive (block 570).

Reference is now made to FIG. 6, which illustrates a system 610 for sensing strain in a structure having an adhesively bonded joint. The system 610 includes a driver 620 for inducing a strain wave in regions of interest in the bonded joint. The driver 620 could be any of a variety of devices that impart a controlled vibration or pulse to a region of interest. In the low frequency approaches, the driver 620 could be located anywhere on the structure and could be far from the region of interest. The higher frequency approaches, such as the piezoelectric transducer, would be directional, and a small, selected region of the bonded joint could be stimulated.

The system 610 further includes a sensor head 630, which may be either handheld or robotically positioned. The sensor head 630 may be a single magnetic sensor that is scanned along the joint, or it may include an array of micromagnetic sensor elements. The micromagnetic sensors could be giant magnetoresistance devices (GMR), tunneling magneto-resistive (TMR) devices, micromagnetic coils, etc. The array is not limited to any particular size or shape or number of sensor elements. The shape of the sensor head 630 may include a flat surface to place against the structure to be inspected. The surface of the sensor head 630 may be resilient and flexible to make intimate contact with the structure on flat or curved surfaces.

The system 610 also includes a magnetic field generating coil 640 for generating an external magnetic field at a region of interest. A non-contacting driving coil 640 operating either at DC or an alternating frequency can create an external magnetic field over the region of interest and it can set the magnetization of the magnetostrictive material.

For those embodiments that correlate the magnetic measurements with measured strain, the system 610 may also include a vibration sensor 655 for measuring vibration at a region of interest. For example, the vibration sensor 655 may include micromechanical, optical or electro-magnetic sensors that record amplitude and delay of a vibration.

The system 610 may further include a controller 650, and a signal processor or computer 660. The controller 650 controls the operation of the driver 620, the sensor head 630, and the field generating coil 640. The signal processor or computer 660 receives outputs from the sensor head 630, and analyzes these outputs to assess the structural health of a bonded joint according to an embodiment herein.

The signal processor or computer 660 may also display a real time strain image on a display 670. This would allow a technician to take a closer look at suspect areas by repeating the measurement or varying the magnetic and mechanical signals (such as changing the frequency or changing the selection of sensor array elements or increasing the integration time for increased sensitivity.)

Figure 7A:
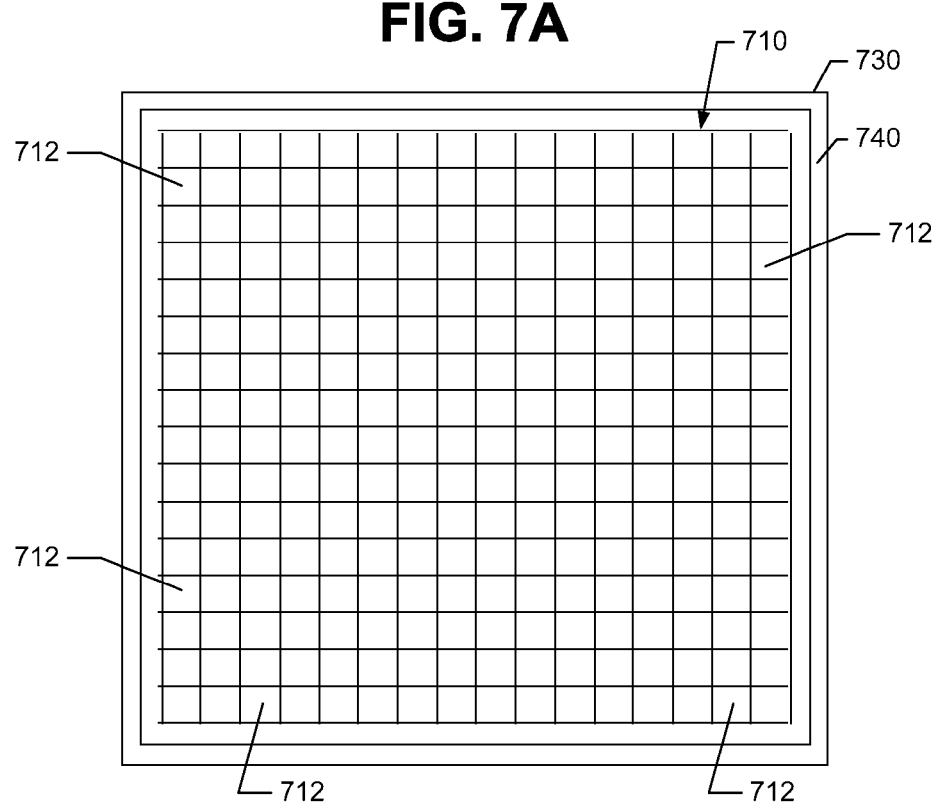
FIGS. 7*a* and 7*b* are illustrations of an array for inducing and sensing a strain wave in an adhesively bonded joint containing strain-sensitive magnetostrictive material.

Reference is now made to FIG. 7a, which illustrates a single array 710 that induces strain waves at regions of interest, generates external magnetic fields at regions of interest, senses vibrations at regions of interest, and senses magnetization at selected regions of interest. Elements 712 of the array 710 includes one or more micromechanical drivers, a plurality of mechanical sensors and a plurality of micromagnetic drivers and micromagnetic sensors. One or more of the micromechanical drivers induce strain waves at selected regions of interest. The micromechanical sensors detect the vibration at selected regions, recording the amplitude and delay of the vibration. For instance, the micromechanical drivers and sensors may include piezo-electric elements that can ultrasonically induce acoustic waves and detect reflected acoustic waves. The piezo-electric elements may be fired using an ultrasonic pulser/receiver and multiplexer as individual elements. The same piezo-electric elements may also be used to sense the vibrations at selected regions of interest.

The micromagnetic drivers (e.g., tiny coils) create the weak external field at selected regions of interest. The micromagnetic sensors detect the amplitude and phase of the strain-affected magnetic responses at the regions of interest. For example, the micromagnetic sensors may include magnetoresistive devices.

Figure 7B:
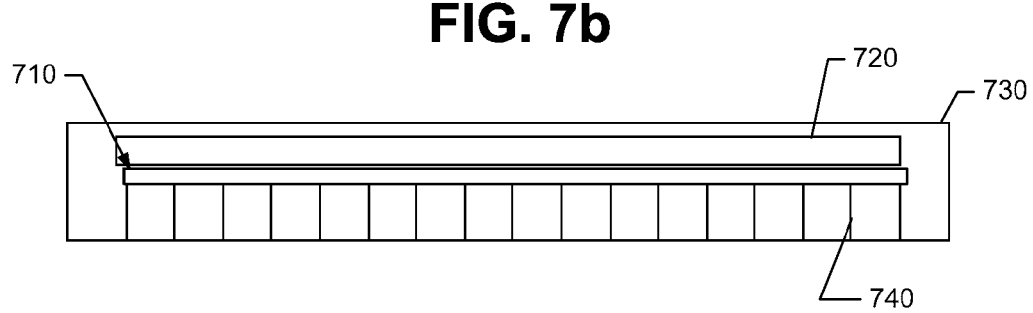

Additional reference is made to FIG. 7b. In embodiments that acoustically induce the strain wave 710, acoustic backing material 720 is provided on one side of the array 710, and a flexible pad 730 is provided on an opposite side of the array 710. The flexible pad 730 may be a poured rubber pad. Such embodiments 710 are flexible, which allows them to match the contour of the structure being inspected. The flexible pad 730 may be provided with segmented delay lines 740 for creating ultrasonic paths for acoustics signals into and out of the array 710.

The flexible pad 730 may be provided with a seal groove 750. The seal groove 750 allows vacuum attach of the pad 730 to the structure being inspected.

A signal processor or computer may be programmed to correlate the magnetic and acoustic signals with each other and with the emitter signal to produce a 2-D or 3-D image of the induced strain in the joint.

Selected elements of the array 710 may be used to perform the method illustrated in FIG. 5a. The correlation of selected multiple sensor elements with the strain signal (that is, using multiple elements to correlate both the magnetic and mechanical vibrations) leads to high resolution and selectivity.

An array is not limited to patterned elements. A first example of an array without patterned elements is illustrated in FIGS. 8-9, and a second example is illustrated in FIG. 10.

Figure 8:
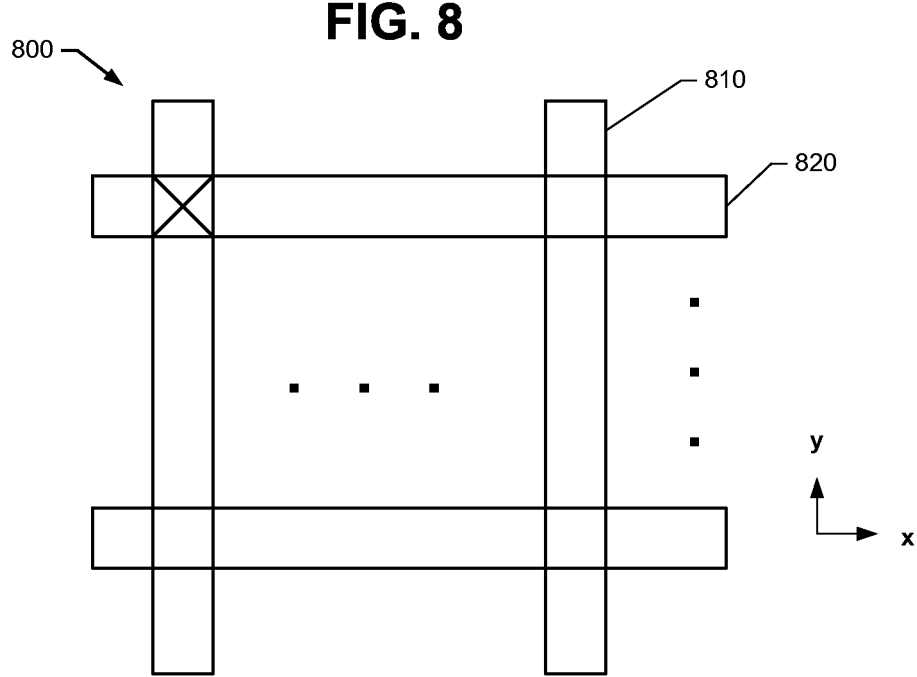
FIGS. 8-9 are illustrations of an array for inducing and sensing a strain wave in an adhesively bonded joint containing strain-sensitive magnetostrictive material.
Figure 9:
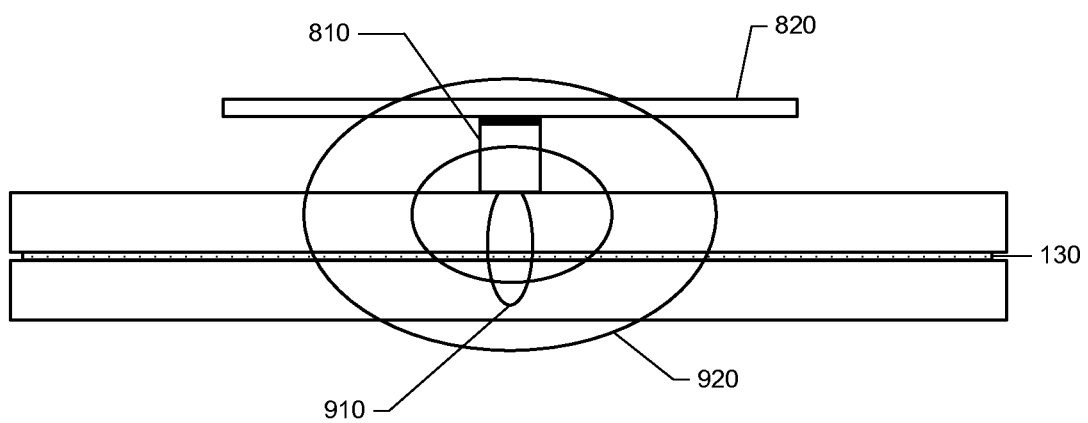
Figure 10:
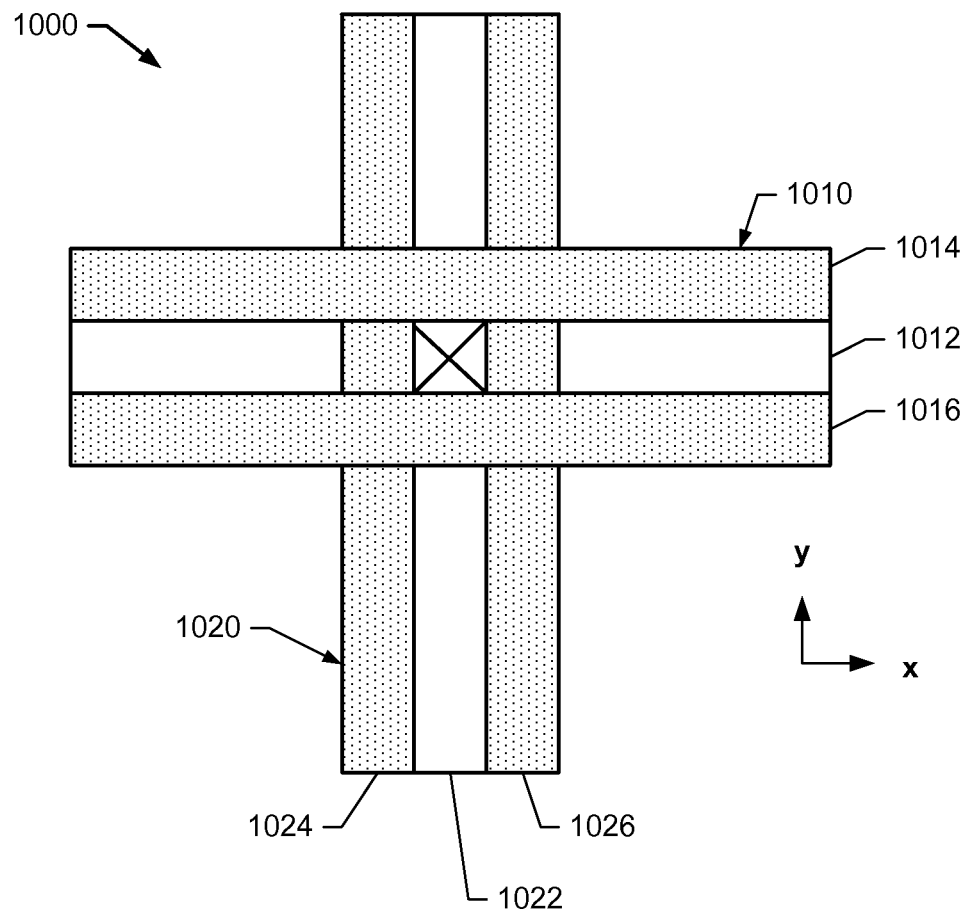
FIG. 10 is an illustration of an array for inducing and sensing a strain wave in an adhesively bonded joint containing strain-sensitive magnetostrictive material.

Reference is now made to FIGS. 8 and 9. An array 800 has two levels of sensor strips: an upper level of micromagnetic sensor strips 820, and a lower level of acoustic strips 810. The acoustic strips 810 extend in a y-direction, and the micromagnetic sensor strips extend in an x-direction. The acoustic strips 810 may be made of transmitting PVDF or other acoustic generation material 810. The micromagnetic sensor strips 820 may be made of magnetic sensor material.

Specific acoustic and magnetic sensor strips 810 and 820 are selected to sense strain beneath a region of interest (marked by an "X" in FIG. 8). A selected acoustic strip 810 may be fired to generate an acoustic strain wave 910 beneath the region of interest. Embedded magnetostrictive particles produce a magnetic field 920 relative to local strains within the adhesively bonded joint 130.

The selected magnetic sensor strip 820, when interrogated, senses the magnetization at the region of interest. The magnetic effects at each magnetostrictive particle are localized and should decrease individually as distance squared. The magnetic signal at the region of interest may be measured and stored as the local strain value at that location. Correlation between the output of the selected acoustic strip 810 (as determined by a calibrated amplitude electro-mechanical amplitude of the transmitting device) and the selected micromagnetic sensor strip 820 (Vmag-Vmech) provides a measurement of the magnetization (and therefore permeability) versus strain at the location of interest.

The acoustic strips 810 may also measure the reflected strain wave response from the bonded joint. This measurement allows direct correlation of various structural features and defects (that produce different reflected acoustic responses) to the strain in the bonded joint.

Figure 11:
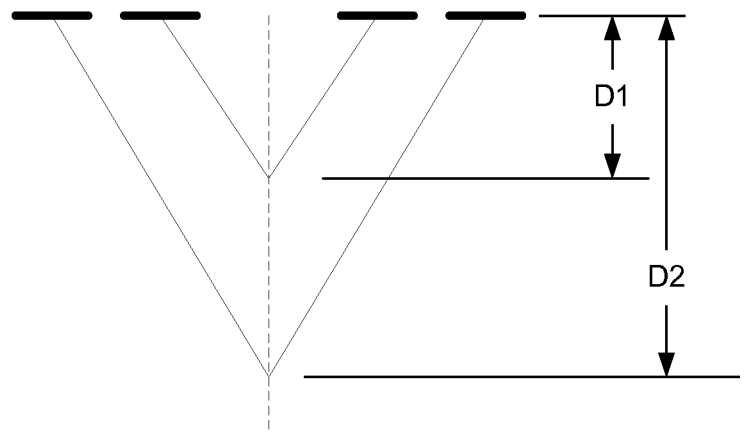
FIG. 11 is an illustration of varying the depth of examination with the array of FIG. 10.

Reference is now made to FIGS. 10-11. An array 1000 has an upper level 1010 of strips and a lower level 1020 of strips. The strips of the upper level extend in an x-direction, and the strips of the lower level extend in a y-direction. Each level includes alternating strips of acoustic material and micromagnetic sensor material. For simplicity, only three strips—a micromagnetic sensor strip 1012 between two acoustic strips 1014 and 1016—is shown in the upper level 1010, and only three strips—a micromagnetic sensor strip 1022 between two acoustic strips 1024 and 1026—is shown in the lower level 1020.

A region of interest is marked by an "X." Examination of the region of interest is performed by selecting two acoustic strips running in one direction (e.g., the x-direction) and selecting one micromagnetic sensor strip running in the orthogonal direction (e.g., the y-direction). The two selected acoustic strips may generate pulses simultaneously or sequentially.

The selected acoustic strips may be switched to inspect the selected region at different depths. As the separation between acoustic strips and micromagnetic sensor strip is increased, the depth of inspection is increased (e.g., from D1 to D2). In this manner, the depth of examination can be varied.

The correlation of the acoustic and magnetic responses reduces background noise of a magnetic-only approach, and increases sensitivity to very small defects or joint weaknesses. This approach also decreases the sensitivity to non-structural magnetic effects (such as varying separation distance between sensors or between the sensors and the adhesive edge). Additionally, the differences in the speed of sound and speed of the magnetic effects (speed of light) can, when correlated with the signals from the arrays of very small magnetic and acoustic or micromechanical sensors, be used to precisely locate the defect. Also, the acoustic strips can be used by themselves to locate the weak area, using typical ultrasonic measurement techniques. For an image-based approach, a correlated signal from each strip is the input of one pixel of a displayed image of the joint. The use of inverse Fourier transform processing and the finite speed of propagation of the mechanical vibration could also provide synthetic aperture techniques for thicker structures. Synthetic aperture techniques take advantage of frequency and time-based features of mechanical or stress waves to locate features deep inside structures.

A system and method herein may be used, without limitation, on adhesively bonded structures, composite structures (where layers can be considered individual bonds), and bonded repairs of composites or metals or hybrids. A system and method herein may be used, without limitation, to perform nondestructive examination of automotive structures, building structures, bridge structures, ship structures, etc. However, a system and method herein can be adapted advantageously for nondestructive examination of aircraft structures.

Figure 12:
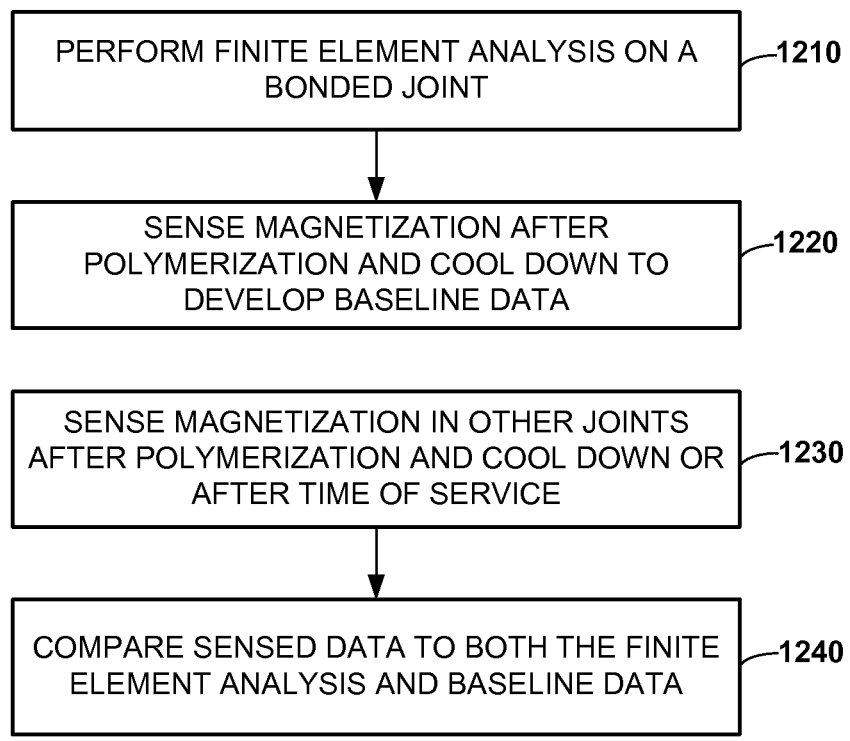
FIGS. 12-14 are illustrations of methods of performing nondestructive examination of an aircraft structure.
Figure 13:
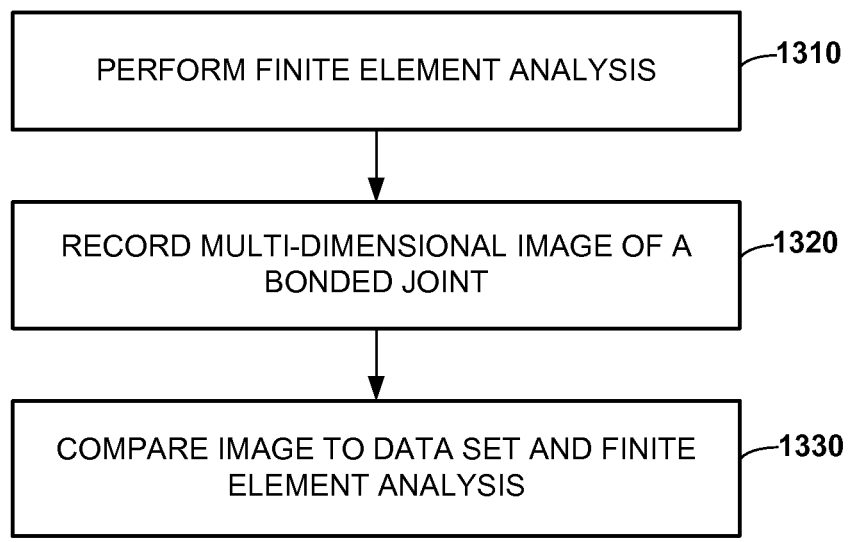
Figure 14:
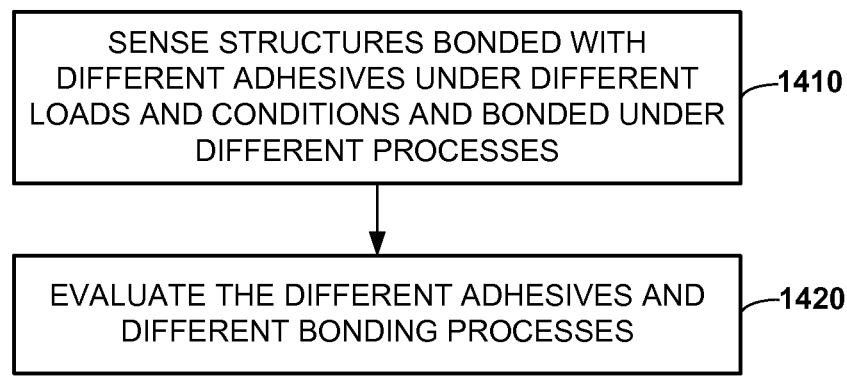

FIGS. 12-14 are illustrations of methods of performing nondestructive examination of an adhesively bonded joint between aircraft structures, where the joint includes strain-sensitive magnetostrictive material. The aircraft structures are not limited to anything in particular. The structures may include elements such as skins, stiffeners, frames and spars. The structures may include major components (or portions thereof) such as wings, fuselage and empennage. The structures may be primary structures or non-primary structures. They may have the same composition (e.g., composite materials, metal, plastic), or they may have different compositions.

In some embodiments, the magnetostrictive material may be applied to an entire bonded joint. In other embodiments, there might be interest in only a region of the adhesive, whereby the magnetostrictive material is applied only to that region. For example, instead of applying magnetostrictive material to an entire bonded joint line, the magnetostrictive material is applied only to those regions where strains are high and where cavitation and debonding are likely to occur. For typical lap joint configurations, one such region is the area under or adjacent to the adhesive fillet.

The methods of FIGS. 12-14 can be used to detect disbonds, delamination and other structural inconsistencies in composite structures of an aircraft. Strain can be sensed without having to attach wires to the aircraft structures, and without having wires stick out of the aircraft structures or the adhesive. Wires sticking out the adhesive are undesirable as they would create a pathway for moisture or fluids from the atmosphere surrounding the joint to move into the interior of the adhesive and thereby increase the chances for premature joint failure.

Reference is made to FIG. 12. The change in magnetization is sensed as part of process control during manufacture. During polymerization and usually cool-down, the polymers shrink, which results in localized variations in strain levels that depend on the bond strength as well as geometry and material properties. The process control may include performing finite element analysis on a joint (block 1210), and sensing the magnetization in the joint after polymerization and cool down to develop baseline data (block 1220). Magnetization is then sensed in other joints of other structures after polymerization and cool down or after time in service (block 1230). The sensed data of the other joints are then compared to both the finite element analysis and baseline data (block 1240). The FEM analysis accounts for differences in geometry and materials, and can represent both the perfect joint and the actual joint. Measurements may be compared to baseline to evaluate aging trends. The comparisons will indicate the presence of contamination, part fit-up issues and uneven pressure during cure. The comparisons may also provide feedback about the manufacture process. The feedback can be used to improve the manufacture process.

Reference is now made to FIG. 13. Changes in magnetization are sensed in real time as part of aircraft health monitoring. Real time sensing of a realistic number of joints (due to practical limitations of weight, access power, memory, etc.) can be performed wherever a probe can be place in close enough proximity. At block 1310, finite element analysis of a joint is performed. At block 1320, the magnetization of a joint may be sensed to record a multi-dimensional (e.g., 2-D or 3-D) image of the joint. At block 1330, this image is compared to a set of data and finite element analysis to determine the state of the joint. As a first example, the data set may include 2-D or 3-D reference images of strain for different loads and conditions. The sensed image is compared to the reference images. The comparison indicates how close localized regions of the joint are to critical strain levels. As a second example, measured strain image is compared to a set of allowable changes. The comparison is performed to identify those bonds that have experienced damage or failure initiation and require repair. The comparison may be performed during flight or during on-ground maintenance, as part of periodic inspections of aircraft structures during scheduled visits to repair depots, etc.

Reference is now made to FIG. 14. Changes in magnetization are sensed to gain a better understanding about adhesive bonds for aircraft structures. Structures bonded with different adhesives or under different bonding processes are sensed under different loads and conditions (block 1410), and the different adhesives or bonding processes are evaluated (block 1420). The evaluation provides strain data, which allows the best adhesive to be selected. This data may be compared to computational simulations to strain throughout structural joints and can be used to design improved structural joints. Data can be accumulated to track the structural integrity of "good" adhesive joints over years of heavy use.

The invention claimed is:

1. An array comprising a plurality of elements for sensing and inducing a strain wave in a selected region of a structure having an adhesively bonded joint, the elements including at least one micromechanical driver for inducing strain waves in selected regions; a plurality of micromagnetic drivers for generating weak magnetic fields over the selected regions; and a plurality of micromagnetic sensors for sensing magnetic responses of the selected regions to the strain waves.

2. The array of claim 1, wherein the micromechanical drivers include strips of acoustic generation material and wherein the micromagnetic sensors include strips of micromagnetic sensor material.

3. The array of claim 2, wherein the strips of acoustic generation material extend in one direction and the strips of micromagnetic sensing material extend in an orthogonal direction.

4. The array of claim 3, further comprising a controller for selecting one of the strips of the acoustic generation material to induce a strain wave, and one of the strips of the micromagnetic sensing material to sense the change in local magnetic characteristics, whereby the selected region is at an intersection of the two selected strips.

5. The array of claim 2, wherein the strips are arranged in an upper level extending in one direction and a lower level extending in an orthogonal direction, each level including alternating strips of acoustic material and micromagnetic sensor material.

6. The array of claim 5, further comprising a controller for selecting two of the strips of acoustic material extending in the one direction to induce the strain wave at a selected region, and one of the strips of micromagnetic sensor material extending in the orthogonal direction to sense the change in local magnetic characteristics of the selected region.

7. The array of claim 6, wherein distance between selected strips of acoustic material is varied to inspect the selected region at different depths.

8. The array of claim 1, wherein the elements further include a plurality of mechanical sensors for measuring vibrations resulting from the induced strain waves.

9. A system comprising the array of claim 1, and a controller for causing the at least one micromechanical driver, micromagnetic drivers and micromagnetic sensors to induce and sense a strain wave in a selected region.

* * * * *